United States Patent [19]

Djuric et al.

[11] Patent Number: 4,954,520

[45] Date of Patent: Sep. 4, 1990

[54] 1,3-DIOXOLANE DERIVATIVES USEFUL IN THE TREATMENT OF INFLAMMATION

[75] Inventors: Stevan W. Djuric, Glenview; Thomas D. Penning, Des Plaines, both of Ill.

[73] Assignee: G. D. Searle & Co., Chicago, Ill.

[21] Appl. No.: 299,366

[22] Filed: Jan. 19, 1989

[51] Int. Cl.$^5$ ................... A61K 31/335; C07D 317/26
[52] U.S. Cl. ...................... 514/467; 549/454
[58] Field of Search ......................... 549/454; 574/467

[56] References Cited

U.S. PATENT DOCUMENTS 4,808,729  2/1989  Deason et al. ..................... 548/454

FOREIGN PATENT DOCUMENTS 0134111  7/1984  European Pat. Off. .
2144422  7/1984  United Kingdom .
2177401  7/1984  United Kingdom .

OTHER PUBLICATIONS

J. Evans et al., Prostaglandins, Leukotrienes and Medicine 23: 167–171 (1986).
R. A. Lewis, et al., J. Clin. Invest. 73: 889–897 (1984).

Primary Examiner—Nicky Chan
Attorney, Agent, or Firm—Mary Jo Kanady; Paul D. Matukaitis; Roger A. Williams

[57] ABSTRACT

The present invention relates to compounds of the formula

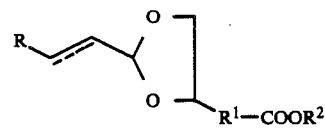

or a pharmaceutically acceptable salt thereof, wherein R is alkyl of 5 to 14 carbon atoms, alkenyl of 5 to 14 carbon atoms or alkynyl of 5 to 14 carbon atoms; $R^1$ is lower alkylene or phenylene; and $R^2$ is hydrogen, lower alkyl or a pharmaceutically acceptable cation.

30 Claims, No Drawings

1,3-DIOXOLANE DERIVATIVES USEFUL IN THE TREATMENT OF INFLAMMATION

BACKGROUND OF THE INVENTION (a) Field of the Invention

The present invention relates to 1,3 dioxolane benzoic acids and derivatives thereof and their pharmaceutically acceptable salts. Compounds of the present invention are useful in treating inflammatory conditions in mammals such as psoriasis, Crohn's disease, ulcerative colitis, arthritis, gout and the like. Compounds of the present invention are inhibitors of leukotriene $B_4$ ($LTB_4$) biosynthesis.

(b) Prior Art $LTB_4$ has been implicated as an important mediator of inflammation due to its potent proinflammatory properties. In neutrophils, $LTB_4$ production from the unstable allylic epoxide $LTA_4$ (Formula I) is catalyzed by a cytosolic enzyme $LTA_4$ hydrolase.

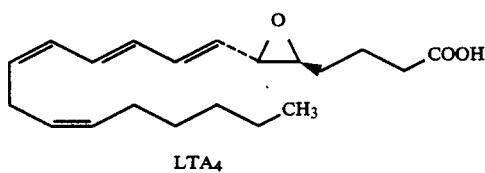

LTA$_4$ $LTB_4$ (Formula II) is an arachidonic acid metabolite which is produced by the 5 lipoxygenase pathway. Pharmacologically, $LTB_4$ is an important mediator of inflammation in mammals. As a mediator of inflammation, $LTB_4$ is known to induce chemotaxis, chemokinesis, aggregation, and degranulation of leukocytes in vitro, and to induce accumulation of polymorphonuclear leukocytes, and increase vascular permeability and edema formation in vivo.

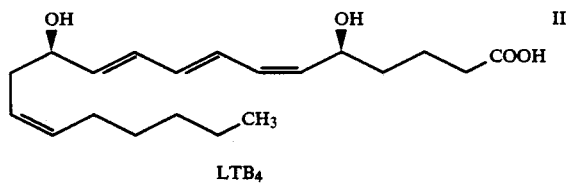

LTB$_4$

Particularly high levels of $LTB_4$ are detected in lesions in inflammatory diseases such as rheumatoid or spondylarthritis, out, psoriasis, ulcerative colitis, Crohn's disease, and some respiratory diseases.

Accordingly, it is an object of this invention to produce compounds for use as pharmaceutical agents which will inhibit $LTB_4$ activity in mammals by inhibiting $LTB_4$ biosynthesis and preventing the formation of $LTB_4$.

U.K. Patent Applications No. GB 2177401 A and GB 2144422 A and their European counterpart EP-134111-A generically disclose compounds of the formula

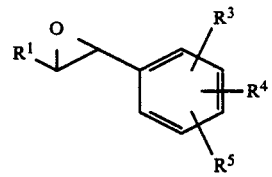

in which $R^1$ is an alkenyl or alkynyl group optionally substituted with an optionally substituted phenyl group and containing from 5 to 30 carbon atoms and, $R^3$, $R^4$, and $R^5$ are each selected from hydrogen, carboxyl $C_{2-5}$ alkoxycarbonyl, $C_{1-4}$ alkyl, $C_{1-4}$ alkoxy, hydroxyl, optionally protected tetrazolyl, halo, trifluoromethyl, nitrile, nitro, and $-CONR_2^{10}$ where each $R^{10}$ is hydrogen or $C_{1-4}$ alkyl. These compounds are intermediates useful for preparing pharmaceutical compounds of the formula

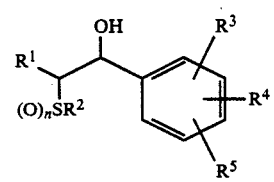

in which n is 0, 1 or 2, $R^1$ is hydrocarbyl group optionally substituted with optionally substituted phenyl group containing from 5 to 30 carbon atoms, $R^2$ is optionally substituted phenyl or $C_{1-10}$ alkyl optionally substituted by one or more substituents selected from optionally protected hydroxyl, optionally protected carboxyl, nitrile, optionally protected tetrazolyl, $-COR^6$ where $R^6$ is $C_{1-4}$alkyl, an optionally protected amino acid residue or $-NR_2^7$ where each $R^7$ is hydrogen or $C_{1-4}$alkyl, and $-NHR^8$ where is hydrogen, a protecting group, an optionally protected amino acid residue, $C_{1-4}$alkyl or $-COR^9$ where $R^9$ is $C_{1-4}$alkyl or $C_{1-4}$alkoxy, and $R^3$, $R^4$ and $R^5$ are each selected from hydrogen, carboxyl, $C_{2-5}$alkoxycarbonyl, $C_{1-4}$alkyl, $C_{1-4}$alkoxy, hydroxyl, optionally protected tetrazoyl, halo, trifluoromethyl, nitrile, nitro and $-CONR_2^{10}$ where each $R^{10}$ is hydrogen or $C_{1-4}$alkyl; and salts thereof. These compounds in unprotected form, are disclosed to be pharmacologically active in tests which demonstrate their antagonist effect on leukotriene receptors and indicate their use in the treatment of allergic disorders.

The pharmacology of the biologically active leukotrienes is generally discussed in J. CLIN. INVEST. 73: 889–897 (1984).

SUMMARY OF THE INVENTION

The present invention relates to compounds of the formula

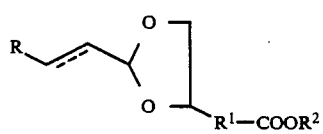

or a pharmaceutically acceptable salt thereof wherein R is alkyl of 5 to 14 carbon atoms, alkenyl of 5 to 14 carbon atoms or alkynyl of 5 to 14 carbon atoms; $R^1$ is lower alkylene or phenylene; and $R^2$ is hydrogen, lower alkyl or a pharmaceutically acceptable cation.

DETAILED DESCRIPTION OF THE INVENTION

This invention encompasses compounds of Formula III as previously described. A preferred embodiment of the present invention encompasses compounds of the formula

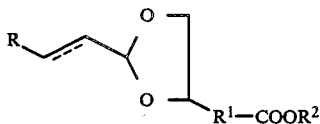

or a pharmaceutically acceptable salt thereof, wherein R is alkyl of 9 to 12 carbon atoms, or alkenyl of 9 to 12 carbon atoms, $R^1$ is alkylene of from 1 to 4 carbon atoms or phenylene; and $R^2$ is hydrogen, alkyl of from 1 to 4 carbon atoms or a pharmaceutically acceptable cation.

More preferred compounds of the present invention are compounds of the formula

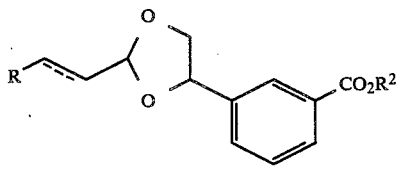

or a pharmaceutically acceptable salt thereof, wherein R is alkyl of 9 to 12 carbon atoms or alkenyl of 9 to 12 carbon atoms; and $R^2$ is hydrogen, alkyl of from 1 to 4 carbon atoms or a pharmaceutically acceptable cation.

The present invention also includes compounds of the formula

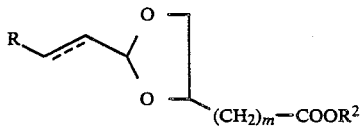

or a pharmaceutically acceptable salt thereof, wherein R is alkyl of 9 to 12 carbon atoms or alkenyl of 9 to 12 carbons; m is 1 to 4; and $R^2$ is hydrogen, alkyl of from 1 to 4 carbon atoms or a pharmaceutically acceptable cation.

The compounds encompassed by the present invention are not limited to any particular stereochemical configuration. Both cis and trans isomers are within the scope of the invention.

The present invention includes pharmaceutical compositions for the treatment of inflammatory conditions in mammals such as psoriasis, Crohn's disease, ulcerative colitis, arthritis, gout, and the like comprising a pharmaceutically acceptable carrier and a compound of Formula III.

The term "lower alkyl" as used to describe $R_1$ and $R_2$ means straight or branched chain alkyls having 1-6 carbon atoms.

The term "aryl" as used to describe $R^1$ means phenyl or substituted phenyl.

The term "pharmaceutically acceptable cations" as used to describe $R^2$ refers to cations such as ammonium, sodium, potassium, lithium, calcium, magnesium, ferrous, zinc, copper, manganous, aluminum, ferric, manganic, tetraalkyl ammonium, and the like.

The term "pharmaceutically acceptable salts" refers to those base derived salts of any compound herein having a carboxylic acid function.

In Formula III and the other structural formulas the dotted line represents an optional bond between the two carbon atoms. Thus the solid and dotted lines (—) indicate that these may be either a single bond or double bond between the two carbon atoms.

The base derived salts can be derived from pharmaceutically acceptable non toxic inorganic or organic bases. Among the inorganic bases employed to produce said pharmaceutically acceptable salts are the hydroxide bases of the "pharmaceutically acceptable cations" disclosed above.

Among the organic bases employed to produce said pharmaceutically acceptable salts are the pharmaceutically acceptable non toxic bases of primary, secondary, and tertiary amines. Especially preferred non-toxic bases are isopropylamine, diethylamine, ethanolamine, dicyclohexylamine, choline, and caffeine. All the pharmaceutically acceptable non toxic addition salts are prepared by conventional processes well known to those of ordinary skill in the art.

The present invention encompasses pharmaceutical compositions containing an effective therapeutic amount of a compound of Formula III along with a pharmaceutically acceptable carrier.

The invention also includes a method of treating inflammatory conditions in animals by administering an anti-inflammatory effective amount of a compound of Formula III.

The compounds described herein may be prepared by any available procedure. The compounds of this invention are generally prepared according to the reaction scheme set out in Scheme A.

As illustrated in Scheme A, an aldehyde (1) is reacted with a dihydroxy alkyl ester (2) in the presence of catalytic pyridinium p toluene sulfonate (PPTS) or p-toluene sulfonic acid monohydrate (TsOH) The reactants are heated in an organic solvent such as benzene to give the dioxolane (3) which may be reacted with lithium hydroxide to give the lithium salt (4). The acid (5) is prepared by adding the lithium salt to ether then neutralizing it with dilute acid such as dilute hydrochloric acid. The product is recovered by extracting the water layer with ether, drying the ether layer over sodium sulfate and removing the ether to give the product.

SCHEME A

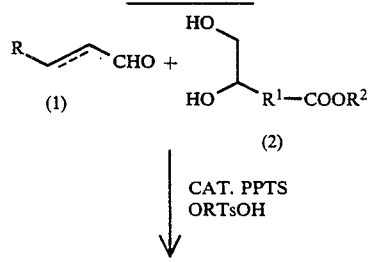

-continued
SCHEME A

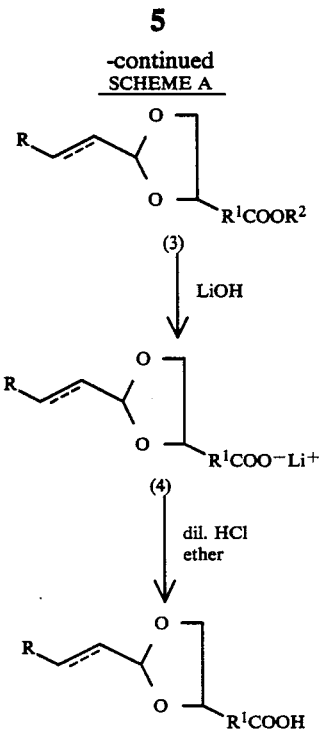

R and R¹ are defined as for Formula III.
R² is alkyl.

Compounds of the present invention are useful by reason of their valuable biological properties. They are inhibitors of LTB₄ biosynthesis and they inhibit the formation of LTB₄ which has been implicated as an important mediator of inflammation due to its potent proinflammatory properties.

Leukotrienes are a class of compounds released by various cell types including neutrophils (PMN) Gillard, J. et al., *Drugs of the Future*, 12:453–474 (1987). Leukotriene biosynthesis is initiated by a lipoxygenase reaction with arachidonic acid to produce 5S-HPETE, which in turn is dehydrated to form leukotriene-A₄ (LTA₄). LTA₄ is the substrate for a cytosolic enzyme, LTA₄ hydrolase which produces LTB₄, a compound with potent pro-inflammatory properties. LTB₄ biosynthesis inhibition with subsequently reduced LTB₄ production may provide a mechanism for preventing or reducing inflammatory responses.

The activity of the compounds of the present invention was determined using the following tests.

A23187-Induced LTB₄ Production in Human Promyelocytic Leukemia HL-60 Cells.

Materials:

Calcium ionophore A23187 was obtained from Calbiochem (La Jolla, CA). Trans-stilbene oxide was obtained from Sigma (St. Louis, MO). Hanks' balanced salt solution (HBSS) (10X concentrate), 1 M Hepes, and Dulbecco's modified Eagle medium were obtained from GIBCO Laboratories (Grand Island, NY). Fetal bovine serum was obtained from HyClone Laboratories (Logan, UT) The LTB₄ and PGE₂ radioimmunoassay antibodies were purchased from Amersham International plc (Amersham, UK) and NEN Research Products (N. Billerica, MA), respectively. Reagents for assay of lactate dehydrogenase (LDH) activity were purchased from Beckman (Carlsbad, CA).

Preparation of HL 60 Cells:

HL-60 cells were cultured in Dulbecco's modified Eagle medium (supplemented with 20% fetal bovine serum, 20 mM Hepes, 100 U/ml penicillin and 100 mcg/ml streptomycin) and maintained at 37° C. in a humidified atmosphere of 5% $CO_2$ in air. Cells from exponentially growing cultures were seeded at $3 \times 10^5$ cells/ml and induced to differentiate into granulocyte with 0.8% (v/v) N,N dimethylformamide for 4 days (1,2). Prior to assay, differentiated HL-60 cells were washed once with Hanks' balanced salt solution containing 0.35 mg/ml sodium bicarbonate and 10 mM Hepes, pH 7.3 (HBSS) and resuspended in HBSS at a concentration of $3 \times 10^6$ cells/ml. HL-60 cell viability was >95% as assessed by trypan blue exclusion.

HL-60 Cell Assay:

DMSO or test compounds as 100X concentrates in DMSO were added in duplicate to 1.0 ml HL-60 cell suspensions ($3 \times 10^6$ cells) and preincubated at 37° C. for 10 minutes in a shaking water bath. After an additional 5 minute incubation with calcium ionophore A23187 (10 mcl @ $5 \times 10^{-4}$M in DMSO), the cells were pelleted at $12,800 \times g$ for 15 seconds and the supernatant removed and stored at 20° C. for quantification of LTB₄ or PGE₂ via radioimmunoassay and LDH activity.

Statistical Methods:

LTB₄ and PGE₂ data were expressed as percent inhibition of A23187-stimulated controls. For IC₅₀ determinations, the 4 parameter logistic model was used where y is the percent inhibition response and X is the log₁₀ concentration of the inhibitor:

$$y = \frac{y_\infty - y_0}{1 + [x/a]^b} + Y_0$$

Nonlinear regression was performed using the SAS (3) procedure NLIN to obtain least squares estimates of the four parameters in the above equation: $y_\infty$ (maximum), $Y_0$ (minimum), a (log₁₀ IC₅₀) and b (slope factor). Increases in mean LDH levels for A23187-stimulated cells in the presence of test compound were tested for significance using a one tailed two sample Student's t-test.

References:

1. Fontana, J. A., D. A. Colbert, and A. B. Deisseroth. Identification of a Population of Bipotent Stem Cells in the HL60 Human Promyelocytic Leukemia Cell Line. *Proc. Nat. Acad. Sci. U.S.A.* 78:3863–3866, 1981.
2. Agins, A. P., A. B. Hollmann, K. C. Agarwal and M. C. Wiemann. Detection of a Novel Cyclooxygenase Metabolite Produced by Human Promyelocytic Leukemia (HL-60) Cells. *Biochem. Biophys. Res. Comm.* 126:143–149, 1985.
3. SAS User's Guide: Statistics, Version 5 Edition, SAS Institute Inc., Cary, NC, 1985.

Results for certain compounds of the present invention are given in Table 1.

TABLE 1

| | HL-60 Cell Assay | | | |
|---|---|---|---|---|
| | IC₅₀ | % Inhibition | | |
| Example No. | (μM) | $10^{-6}$ M | $10^{-5}$ M | $10^{-4}$ M |
| 8B | — | — | 1 | 84 |
| 5B (Racemic Mixture | 6.8 | 1 | 80 | 96 |
| 5B (Single Diastereomer) | 7.2 | 1 | 77 | 91 |
| 7B (Racemic Mixture | 2.5 | 21 | 91 | 89 |
| 7B (Single | 3.6 | 1 | 92 | 92 |

TABLE 1-continued

| | HL-60 Cell Assay | | | |
|---|---|---|---|---|
| | IC$_{50}$ | % Inhibition | | |
| Example No. | (μM) | 10$^{-6}$ M | 10$^{-5}$ M | 10$^{-4}$ M |
| diastereomer) | | | | |

I = inactive at that concentration

The compounds can be administered in such oral dosage forms as tablets, capsules, softgels, pills, powders, granules, elixirs, or syrups. The compounds may also be administered intravascularly, intraperitoneally, subcutaneously, intramuscularly, or topically using forms known to the pharmaceutical art. In general, the preferred form of administration is oral or in such a manner so as to localize the inhibitor. In an inflammatory condition such as rheumatoid arthritis, the compounds could be injected directly into the affected joint.

For the orally administered pharmaceutical compositions and methods of the present invention the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate mannitol, and the like, or various combinations thereof. For oral administration in liquid forms, such as in softgels, elixirs, syrups, drops and the like, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, intramuscular or aerosol administration, active drug components may be combined with a suitable carrier such as water, saline, aqueous dextrose, and the like. Regardless of the route of administration selected, the compounds of the present invention are formulated into pharmaceutically acceptable dosage forms by conventional methods known to those skilled in the art. The compounds may also be formulated using pharmacologically acceptable base addition salts. Morever, the compounds or their salts may be used in a suitable hydrated form.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including type, age, weight, sex, and medical condition of the patient, the severity of the inflammatory condition on, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples, temperatures are given in degrees celcius (°C.) and quantities of materials in grams and milliliters unless otherwise noted.

In the following examples, and throughout this application, a wavey line (∼) defines a substituent as having optional R or S stereochemistry. A triangular shaped line (▷) defines the substituent at the base of the triangle as coming out of the plane of the paper, whereas a substituent at the apex of the broken triangle, is defined as going into the plane of the paper.

EXAMPLE 1

5-Hexenoic acid

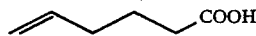

5 Hexene-1-ol (5.0 g. 49.9 mmol) in 10 ml of acetone was added in portions to a cooled solution of 55 ml of 1.33 M Jones reagent (73.2 mmol) in 100 ml of acetone. The mixture was stirred at RT for 3 hours then decanted into diethyl ether/saturated sodium bisulfite. The ether layer was concentrated, and the residue was poured into ether/water. The ether layer was washed with water and with saturated sodium chloride then dried over sodium sulfate and concentrated to provide 5.05 g (44.2 mmol), 89% of the title compound as a colorless oil.

$^1$H NMR (CDCl$_3$) δ5.80 (m, 1H), 5.03 (m, 2H), 2.37 (t, 2H), 2.12 (m, 2H), 1.75 (p, 2H).

EXAMPLE 2

Methyl 5-Hexenoate

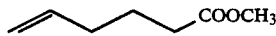

5-Hexenoic acid (4.9 g, 42.9 mmol) was refluxed in 80 ml of methanol with catalytic p toluene sulfonic acid monohydrate for 40 hours. The solution was cooled and concentrated then poured into ether/water. The ether layer was dried over sodium sulfate and concentrated to give 4.6 g (35.9 mmol), 84% of the title compound.

$^1$H NMR (CDCl$_3$) δ5.78 (m, 1H), 5.01 (m, 2H), 3.67 (s, 3H), 2.32 (t, 2H), 2.09 (q, 2H), 1.74 (p, 2H).

EXAMPLE 3

Methyl 5,6-Dihydroxy hexanoate

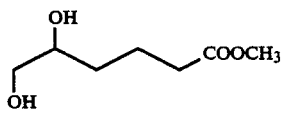

Methyl 5-hexenoate (4.3 g, 33.5 mmol) and 0.29 mmol of osmium tetroxide in t-butyl alcohol (15 ml of a 1g $OsO_4$/200 ml t butyl alcohol solution) were stirred in 60 ml of tetrahydrofuran (THF) and 20 ml of acetone. Trimethylamine-N-oxide dihydrate (4.5 g, 40.5 mmol) in 6 ml of water was added. The black mixture was stirred at room temperature (RT) for 27 ½hours then concentrated and poured into aqueous sodium bisulfite/ethyl acetate. The aqueous layer was washed 3 times with ethyl acetate and the combined ethyl acetate layers were dried over sodium sulfate and concentrated to give 4.1 g of crude product. The crude product was flash chromatographed on silica gel using 100% ethyl acetate as eluent to give 3.24 g (19.98 mmol) 60% of the title compound.

$^1$H NMR (CDCl$_3$) δ3.80–3.20 (m, 5H), 3.68 (s, 3H), 2.37 (t, 2H), 1.76 (m, 2H), 1.45 (q, 2H).

EXAMPLE 4

2E,4E-Pentadecadienal

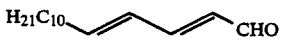

Tributyl (2-ethoxyvinyl) stannane (6.4 g, 17.7 mmol) was stirred in 45 ml of THF and cooled to −78° C. 1.6 M Butyl lithium (10 ml, 16 mmol) was added and the mixture was stirred at −78° C. for 1 hour. 2E-tridecenal (3.0 g, 15.3 mmol) in 5 ml of THF was added, and the mixture was stirred for 1 hour at −78° C. The reaction was stirred with 5 ml of aqueous sodium bicarbonate for 5 minutes, then the organic layer was separated, washed with saturated sodium chloride, dried over sodium sulfate and concentrated to give the crude product. The crude product was flash chromatographed o silica gel using first hexane, then 100:1 to 10:1 hexane/ethyl acetate gradient as eluent to give the title compound (2.4 g, 10.8 mmol) 70.6%.

$^1$H NMR (CDC1$_3$) δ9.12 (d, J=8.0 Hz, 1H), 7.08 (dd, J$_1$=15.3 Hz, J$_2$=9.9 Hz, 1H), 6.32 (m, 2H), 6.08 (dd, J=15.3 Hz, J$_2$=8.0 Hz, 1H), 2.20 (q, 2H), 1.60–1.00 (m, 16H), 0.87 (t, 3H).

EXAMPLE 5A

Methyl 2-tetradeca-1E,3E-dienyl-1,3-dioxolane-4-butanoate

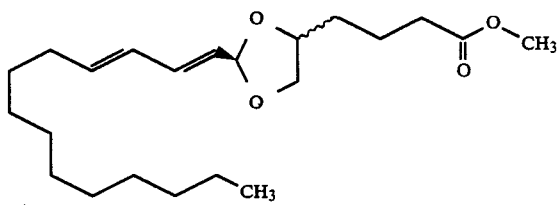

Methyl 5,6-dihydroxyhexanoate (0.32 g, 2.0 mmol)-,2E,4E -pentadecadienal (0.445 g, 2.0 mmol) and catalytic pyridinium p-toluene sulfonate (PPTS) were re-fluxed in 10 ml of benzene with a Dean Stark trap for 21 hours. The mixture was cooled, filtered, and concentrated. Flash chromatography with 25:1+20:1 hexane/ethyl acetate provided methyl 2-tetradeca-1E,-3E-dienyl-1, 3-dioxolane-4-butanoate as 21 mg of isomer B as a crystalline solid, 25 mg of isomer A, as a crystalline solid, and 68 mg of a mixture of A and B.

| Analysis of the mixture: Calculated for $C_{22}H_{38}O_4$ | | |
|---|---|---|
| | C | H |
| Calculated | 72.09 | 10.45 |
| Found | 72.30 | 10.66 |

EXAMPLE 5B

2-Tetradeca-1E,3E-dienyl-1,3-dixolane-4-butanoic acid, lithium salt

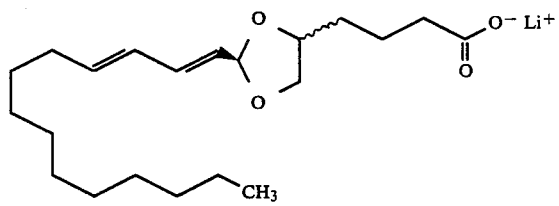

The lithium salt of isomer B and of the mixture of A and B was prepared by reacting 5 mg of the ester in 1 ml methanol and 0.10 ml of 1 N aqueous lithium hydroxide at room temperature for 24 hours. Concentration yielded the crude lithium salt.

EXAMPLE 6

Methyl 3-(1,2-dihydroxyethyl)benzoate

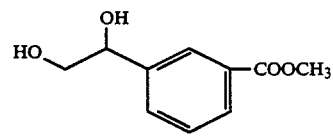

Methyl 3-ethenylbenzoate (0.75 g, 4.62 mmol) and 2.0 ml of a solution of 1.0 g osmium tetroxide in 200 ml of butyl lithium (0.039 mmol) were stirred in 10 ml (THF) and 2 ml acetone. Trimethylamine N oxide (0.62 g, 5.6 mmol) in 1.0 ml of water was added. The mixture was stirred at room temperature for 26 hours then poured into saturated sodium bisulfite/ethyl acetate. The aqueous layer was washed 4 times with ethyl acetate. The combined ethyl acetate layers were dried over sodium sulfate, stirred with decolorizing carbon, filtered and concentrated. Flash chromatography on silica gel with a 10:1 hexane/ethyl acetate to 100% ethyl acetate gradient gave 0.64 g of the title compound (3.26 mmol), 70.6% as a colorless, viscous oil.

| Analysis calculated for $C_{10}H_{12}O_4$. | | |
|---|---|---|
| | C | H |
| Calculated | 61.22 | 6.16 |
| Found | 60.82 | 6.47 |

EXAMPLE 7A

Methyl 3-(2-tetradeca-1E,3E-dienyl-1,3-dixolan-4-yl) benzoate

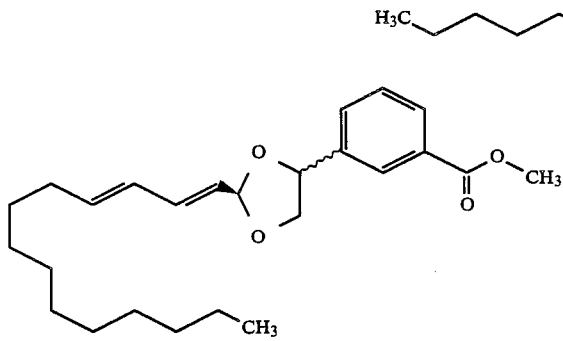

Methyl 3-(1,2-dihydroxy ethyl)benzoate (0.12 g, 0.61 mmol) and 2E,4E-pentadecadienal (0.136 g. 0.61 mmol) were refluxed in 5 ml of benzene with catalytic PPTS for 21 ½ hours in the presence of magnesium sulfate (about 0.5 g). The reaction mixture was filtered and concentrated then flash chromatographed on silica gel using a 100:1 to 20:1 hexane/ethyl acetate gradient to give the title ester as:
(1) isomer A (0.38 g, 0.95 mmol, 15.5 %, oil);
(2) isomer B (0.42 g, 0.105 mmol, 17.2%, waxy solid, m.p. 34°–35.5° C.)
(3) Mixture of isomer A and isomer B (0.31 g, 0.077 mmol, 12.7%)

| Analysis of A,B mixture: Calculated for C<sub>25</sub>H<sub>36</sub>O<sub>4</sub> | | |
|---|---|---|
|  | C | H |
| Calculated | 74.96 | 9.06 |
| Found | 74.69 | 9.44 |

EXAMPLE 7B 3-(2-Tetradeca-1E,3E-dienyl-1,3-dioxolan-4-yl)benzoic acid, lithium salt

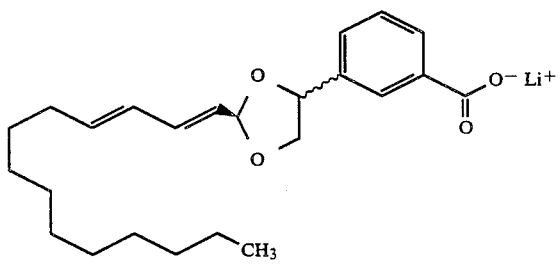

Reaction of the ester with lithium hydroxide using the procedure described in Example 5B gave the lithium salt.

EXAMPLE 8A (±) Methyl 2-undeca-1E,3E-dienyl-1,3-dioxolane-4-butanoate

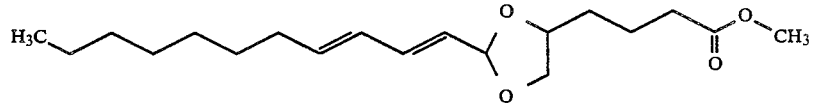

Methyl 5,6-dihydroxyhexanoate (0.32 g, 2.0 mmol), 2E,4E-dodecadienal and catalytic pyridinium p-toluenesulfonate (PPTS) were refluxed in 10 ml of benzene for 39 hours with a Dean-Stark trap. Molecular sieves were added after 19 hours. The reaction mixture was cooled, filtered and concentrated. Flash chromatography on silica gel with 25:1 hexane/ethyl acetate as eluent gave the product (0.10 g, 0.31 mmol), 15%.

| Analysis calculated for C<sub>19</sub>H<sub>32</sub>O<sub>4</sub> | | |
|---|---|---|
|  | C | H |
| Calculated | 70.33 | 9.94 |
| Found | 70.35 | 9.96 |

EXAMPLE 8B (±) 2-Undeca-1E,3E-dienyl-1,3-dioxolane-4-butanoic acid, lithium salt

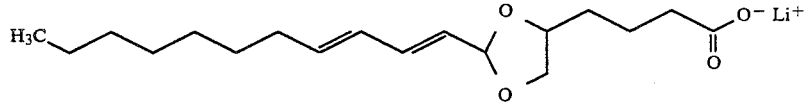

Reaction of the ester with lithium hydroxide using the procedure described in Example 5B gave the lithium salt.

What is claimed is:

1. A compound of the formula

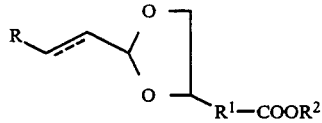

or a pharmaceutically acceptable salt thereof, wherein R is alkyl of 5 to 14 carbon atoms, alkenyl of 5 to 14 carbon atoms or alkynyl of 5 to 14 carbon atoms; $R^1$ is lower alkylene or phenylene; and $R^2$ is hydrogen or lower alkyl.

2. A compound according to claim 1 of the formula

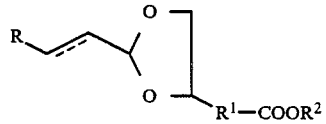

or a pharmaceutically acceptable salt thereof, wherein R is alkyl of 9 to 12 carbon atoms, or alkenyl of 9 to 12 carbon atoms, $R^1$ is alkylene of from 1 to 4 carbon atoms or phenylene; $R^2$ is hydrogen or alkyl of from 1 to 4 carbon atoms.

3. A compound according to claim 2 of the formula

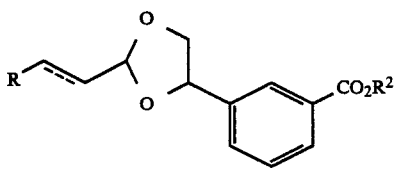

or a pharmaceutically acceptable salt thereof, wherein R is alkyl of 9 to 12 carbon atoms or alkenyl of 9 to 12 carbon atoms; and $R^2$ is hydrogen or alkyl of from 1 to 4 carbon atoms.

4. A compound according to claim 2 of the formula

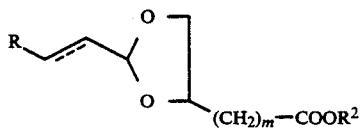

or a pharmaceutically acceptable salt thereof, wherein R is alkyl of 9 to 12 carbon atoms or alkenyl of 9 to 12 carbons; m is 1 to 4; and $R^2$ is hydrogen or alkyl of from 1 to 4 carbon atoms.

5. A compound according to claim 3 which is methyl 3-(2-tetradeca-1E,3E-dienyl-1,3-dioxolan-4-yl) benzoate.

6. A compound according to claim 3 which is 3-(2-tetradeca-1E,3E-dienyl-1,3-dioxolan-4-yl)benzoic acid, lithium salt.

7. A compound according to claim 4 which is methyl 2-tetradeca-1E,3E-dienyl-1,3-dioxolane-4-butanoate.

8. A compound according to claim 4 which is 2-tetradeca-1E,3E-dienyl-1,3-dioxolane-4-butanoic acid, lithium salt.

9. A compound according to claim 4 which is (±)methyl 2-undeca-1E,3E-dienyl-1,3-dioxolane-4-butanoate.

10. A compound according to claim 4 which is (±)2-undeca-1E,3E- dienyl-1,3-dioxolane-4-butanoic acid, lithium salt.

11. A pharmaceutical composition for the treatment of inflammatory diseases comprising a therapeutically effective amount of a compound of the formula

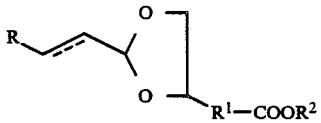

or a pharmaceutically acceptable salt thereof, wherein R is alkyl of 5 to 14 carbon atoms, alkenyl of 5 to 14 carbon atoms or alkynyl of 5 to 14 carbon atoms; $R^1$ is lower alkylene or phenylene; and $R^2$ is hydrogen, lower alkyl; and a pharmaceutically acceptable carrier.

12. A pharmaceutical composition according to claim 11 for the treatment of inflammatory disease comprising a therapeutically effective amount of a compound of the formula

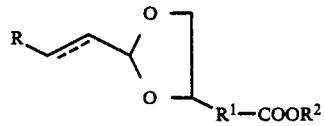

or a pharmaceutically acceptable salt thereof, wherein R is alkyl or 9 to 12 carbon atoms, or alkenyl of 9 to 12 carbon atoms, $R^1$ is alkylene of from 1 to 4 carbon atoms or phenylene; $R^2$ is hydrogen or alkyl of from 1 to 4 carbon atoms; and a pharmaceutically acceptable carrier.

13. A pharmaceutical composition according to claim 12 for the treatment of inflammatory disease comprising a therapeutically effective amount of a compound of the formula

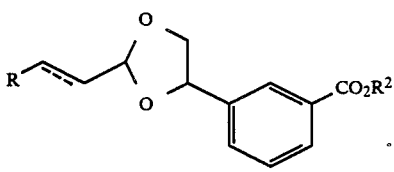

or a pharmaceutically acceptable salt thereof, wherein R is alkyl of 9 to 12 carbon atoms or alkenyl of 9 to 12 carbons; and $R^2$ is hydrogen or alkyl of from 1 to 4 carbon atoms; and a pharmaceutically acceptable carrier.

14. A pharmaceutical composition according to claim 12 for the treatment of inflammatory disease comprising a therapeutically effective amount of a compound of the formula

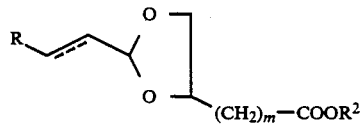

or a pharmaceutically acceptable salt thereof wherein R is alkyl of 9 to 12 carbon atoms or alkenyl of 9 to 12 carbons; m is 1 to 4; $R^2$ is hydrogen or alkyl of from 1 to 4 carbon atoms; and a pharmaceutically acceptable carrier.

15. A pharmaceutical composition according to claim 13 wherein said compound is methyl 3-(2-tetradeca-1E, 3E-dienyl-1,3-dioxolan-4-yl) benzoate.

16. A pharmaceutical composition according to claim 13 wherein said compound is 3-(2-tetradeca-1E, 3E-dienyl-1,3-dioxolan-4-yl)benozoic acid, lithium salt.

17. A pharmaceutical composition according to claim 14 wherein said compound is methyl 2-tetradeca-1E, 3E-dienyl-1,3-dioxolane-4-butanoate.

18. A pharmaceutical composition according to claim 14 wherein said compound is 2-tetradeca-1E, 3E-dienyl-1,3-dioxolane-4-butanoic acid, lithium salt.

19. A pharmaceutical composition according to claim 14 wherein said compound is (±) methyl 2-undeca-1E, 3E-dienyl-1,3-dioxolane-4-butanoate.

20. A pharmaceutical composition according to claim 14 wherein said compound is (±) 2-undeca-1E,3E-dienyl-1,3-dioxolane-4-butanoic acid, lithium salt.

21. A method of treating inflammatory diseases comprising administering to a mammal in need of such treatment a therapeutically effective amount of a compound of the formula

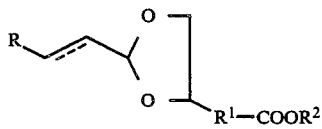

or a pharmaceutically acceptable salt thereof, wherein R is alkyl of 5 to 14 carbon atoms, alkenyl of 5 to 14 carbon atoms or alkynyl of 5 to 14 carbon atoms; $R^1$ is lower alkylene or phenylene; and $R^2$ is hydrogen or lower alkyl.

22. A method according to claim 21 wherein said compound is of the formula

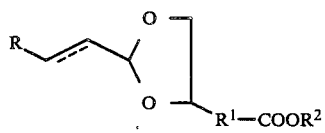

or a pharmaceutically acceptable salt thereof, wherein R is alkyl of 9 to 12 carbon atoms, or alkenyl of 9 to 12 carbon atoms; $R^1$ is alkylene of from 1 to 4 carbon atoms or phenylene; and $R^2$ is hydrogen or alkyl of from 1 to 4 carbon atoms.

23. A method according to claim 22 wherein said compound is of the formula

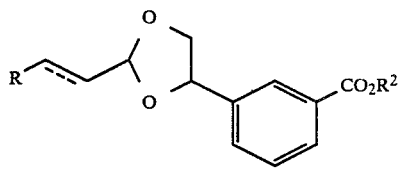

or a pharmaceutically acceptable salt thereof, wherein R is alkyl of 9 to 12 carbon atoms or alkenyl of 9 to 12 carbon atoms; and $R^2$ is hydrogen or alkyl of from 1 to 4 carbon atoms.

24. A method according to claim 22 wherein said compound is of the formula

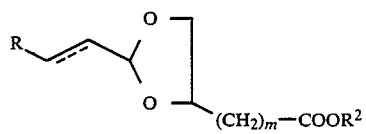

or a pharmaceutically acceptable salt thereof, wherein R is alkyl of 9 to 12 carbon atoms or alkenyl of 9 to 12 carbons; m is 1 to 4; and $R^2$ is hydrogen or alkyl of from 1 to 4 carbon atoms.

25. A method according to claim 23 wherein said compound is methyl 3-(2-tetradeca-1E,3E-dienyl-1,3-dioxolan-4-yl)benozoate.

26. A method according to claim 23 wherein said compound is 3-(2-tetradeca-1E,3E-dienyl-1,3-dioxolan-4-yl)benzoic acid, lithium salt.

27. A method according to claim 24 wherein said compound is methyl 2-tetradeca-1E,3E-dienyl-1,3-dioxolane-4-butanoate.

28. A method according to claim 24 wherein said compound is 2-tetradeca-1E,3E-dienyl-1,3-dioxolane-4-butanoic acid, lithium salt.

29. A method according to claim 24 wherein said compound is (±) methyl 2-undeca-1E,3E-dienyl-1,3-dioxolane-4-butanoate.

30. A method according to claim 24 wherein said compound is (±) 2-undeca-1E,3E-dienyl-1,3-dioxolane-4-butanoic acid, lithium salt.

* * * * *

UNITED STATES PATENT AND TRADEMARK OFFICE
CERTIFICATE OF CORRECTION

PATENT NO. : 4,954,520

DATED : September 4, 1990

INVENTOR(S) : Djuric et al.

It is certified that error appears in the above-identified patent and that said Letters Patent is hereby corrected as shown below:

Column 1, line 57, reading "out" should read -- gout --.
Column 2, line 36, reading "$C_{1-4}$alkyl" should read
-- $C_{1-4}$alkyl, $C_{1-4}$alkoxy --.

Column 2, line 38, reading "where is" should read -- where $R^8$ is --.
Column 3, line 18, reading "carbOn" should read -- carbon --.
Column 6, line 23, reading "20°C." should read -- -20°C. --.
Column 6, line 34, reading "y0" should read -- $y_0$ --.
Column 8, line 62, reading "p toluene" should read
-- p-toluene --.
Column 13, line 62, reading "hydrogen, lower" should read
-- hydrogen or lower --.

Signed and Sealed this

Twelfth Day of May, 1992

*Attest:*

DOUGLAS B. COMER

*Attesting Officer*  *Acting Commissioner of Patents and Trademarks*